(12) United States Patent
Macaluso et al.

(10) Patent No.: US 9,918,671 B2
(45) Date of Patent: Mar. 20, 2018

(54) SWEAT MEASUREMENT DEVICE

(71) Applicant: Stellenbosch University, Stellenbosch, Western Cape Province (ZA)

(72) Inventors: Filippo Macaluso, Cefalù (IT); Kathy Helen Myburgh, Western Cape (ZA)

(73) Assignee: Stellenbosch University, Stellenbosch, Western Cape Province (ZA)

( * ) Notice: Subject to any disclaimer, the term of this patent is extended or adjusted under 35 U.S.C. 154(b) by 387 days.

(21) Appl. No.: 14/400,135

(22) PCT Filed: May 29, 2013

(86) PCT No.: PCT/IB2013/054440
§ 371 (c)(1),
(2) Date: Nov. 10, 2014

(87) PCT Pub. No.: WO2013/179240
PCT Pub. Date: Dec. 5, 2013

(65) Prior Publication Data
US 2015/0141775 A1    May 21, 2015

(30) Foreign Application Priority Data
May 29, 2012 (ZA) .................................. 2012/03894

(51) Int. Cl.
*A61B 5/00* (2006.01)
*A61B 10/00* (2006.01)

(52) U.S. Cl.
CPC .......... *A61B 5/4266* (2013.01); *A61B 5/6824* (2013.01); *A61B 5/6833* (2013.01); *A61B 10/0064* (2013.01); *A61B 5/4875* (2013.01)

(58) Field of Classification Search
CPC . A61B 5/4266; A61B 5/6833; A61B 10/0064; A61B 5/6824; A61B 5/4875
See application file for complete search history.

(56) References Cited

U.S. PATENT DOCUMENTS 4,542,751 A * 9/1985 Webster ............... A61B 5/4266
600/308
2003/0091472 A1   5/2003 Cremerius et al.
(Continued)

FOREIGN PATENT DOCUMENTS

EP        0861639 A2   9/1998
JP     2010046196 A  * 3/2010

OTHER PUBLICATIONS

English Machine Translation of JP 2010046196 A.*
(Continued)

*Primary Examiner* — Navin Natnithithadha
*Assistant Examiner* — Andrey Shostak
(74) *Attorney, Agent, or Firm* — Bret E. Field; Bozicevic, Field & Francis LLP

(57) ABSTRACT

A sweat measuring device (1) comprising a sweat impermeable panel (40) and an adhesive skirt on one side thereof extending about its periphery to enable the panel to be secured to a user's skin is provided. The device covers a known area of a user's skin and traps sweat (42) produced by the skin under the panel. The panel (40) defines a reservoir in which sweat can accumulate and calibrations which may be associated with the reservoir to express the total sweat produced by the user as a function of the volume of sweat in the reservoir. The panel may be relatively stiff; formed by a plastics member and the skirt may extend integrally from the panel or be provided by an adhesive patch which covers the panel.

13 Claims, 2 Drawing Sheets

(56) References Cited

U.S. PATENT DOCUMENTS

2007/0179373 A1* 8/2007 Pronovost ............ A61B 5/1486
600/362
2010/0132485 A1* 6/2010 Erez .................... A61B 5/4266
73/863.11

OTHER PUBLICATIONS

Appenzeller et al., Determination of the volume of sweat accumulated in a sweat-patch using sodium and potassium as internal reference, J Chromatogr B Analyt Technol Biomed Life Sci (2007), 852(1-2):333-337.
"Sweat Rate Measurement"—http://www.topendsports.com/testing/tests/hydration-sweat-rate.htm, Accessed on Jan. 27, 2015, 2 pages.
Appenzeller et al., "Determination of the volume of sweat accumulated in a sweat-patch using sodium and potassium as internal reference", J Chromatogr B Analyt Technol Biomed Life Sci (2007), 852(1-2):333-337.
"Sweat Rate Measurement", Mar. 21, 2012, XP055077745, www.topendsports.com, Retrieved from the Internet: URL: http://web.archive.org/web/20120321235507/http://www.topendsports.com/testing/tests/hydration-sweat-rate.htm.

\* cited by examiner

SWEAT MEASUREMENT DEVICE

FIELD OF THE INVENTION

This invention relates to a device for measuring sweat produced by a user.

BACKGROUND TO THE INVENTION

Sweat, or perspiration, is often produced during physical activity and, to keep the body functioning optimally, lost fluids have to be replenished. For sports people it is particularly important to ensure adequate hydration. However, it is known that drinking too much fluid can be detrimental, possibly even more so than drinking too little fluids.

As individuals sweat at different rates, and sweating also depends on climatic conditions and the individual's level of activity, it can be quite difficult to accurately estimate the amount of fluid required at any given time to maintain proper hydration for individuals engaged in physical activities. Such activities include sport, work and military activities. Proper hydration is particularly important where the activities take place in deserts and other hot or high humidity environments.

It is also critical with some diseases which can induce high levels of dehydration, such as malaria, that hydration be carefully monitored and controlled.

Methods of measuring sweat production are available, but are typically quite complex. These methods mostly rely on measurements of conductivity on the skin and hence require electronic equipment to function. As such, these devices are fairly complex and may be difficult to use during normal sporting events or by many individuals simultaneously.

A method of measuring sweat, described in JP 2010-046196A, uses an elongate body of absorbent material to draw up sweat produced by a wicking action. In order to measure the sweat production, the absorbent material is impregnated with a colour indicator which changes colour when a certain amount of sweat is collected. This device is therefore reliant on chemical changes as well the use of materials having the correct properties to allow incorporation of chemical indicators thereon while retaining its wicking abilities in order to be effective. It also implies a single use.

SUMMARY OF THE INVENTION

A sweat measuring device comprising a sweat impermeable panel which covers a known area of a user's skin and has a skirt with an adhesive on one side thereof extending about its periphery to enable the panel to be secured to a user's skin to trap sweat produced by the skin under the panel and wherein the panel defines a reservoir in which sweat can accumulate and the level of which can be visually inspected against calibrations associated with the reservoir.

Further features of the invention provide for the calibrations to express the total sweat produced by the user as a function of the level of sweat in the reservoir.

Still further features of the invention provide for the reservoir to be tubular and extend, in use, in a generally upright direction; alternately for the panel to be convex or have at least one spacer to space it apart from the skin to so form the reservoir.

Yet further features of the invention provide for the panel to be relatively stiff; and for the panel to be formed by a plastics member.

Further features of the invention provide for the skirt to extend integrally from the panel; alternately for the skirt to be provided by an adhesive patch which covers the panel.

Further features of the invention provide for the calibrations associated with the reservoir to be in the form of markings, for the markings to be in the form of labels, indentations or protrusions on the sweat measuring device; or provided on an adhesive strip which may be attached to the sweat measuring device.

The invention also provides a method of measuring sweat produced by a user which includes collecting sweat in a reservoir from a patch of skin of known area over a period of time such that the level of the collected sweat can be visually inspected against calibrations associated with the reservoir to determine the amount of collected sweat and expressing the amount of collected sweat as a proportion of sweat produced for an entire body associated with the skin.

BRIEF DESCRIPTION OF THE DRAWINGS

The invention will now be described, by way of example only with reference to the accompanying representations in which.

DETAILED DESCRIPTION WITH REFERENCE TO THE DRAWINGS

Figure 1:
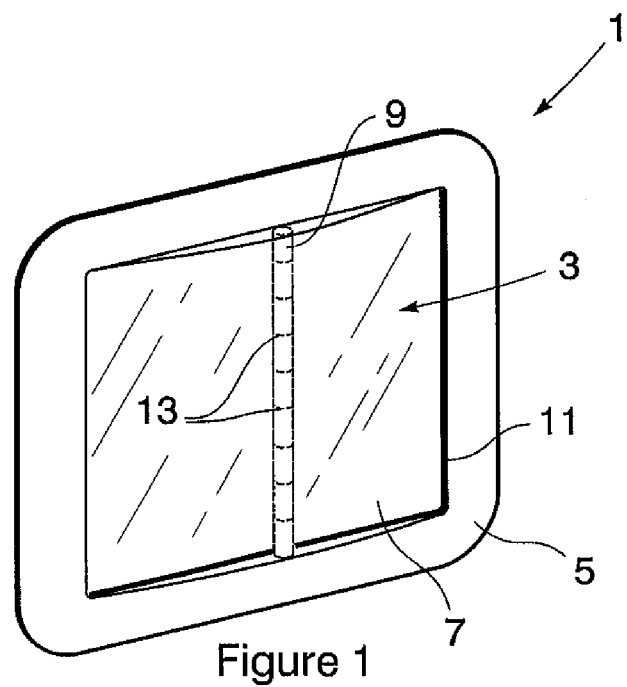
FIG. 1 is perspective view of a first embodiment of a sweat measuring device.

A sweat measuring device (1) is shown in FIG. 1 and includes a sweat impermeable panel (3) having a skirt (5) which extends about its periphery. In this embodiment, the panel (3) includes a stiff, generally rectangular, transparent plastics sheet (7) with a transparent plastics tube (9) secured thereto and extending centrally along its length on one side of the sheet (7). An adhesive film (11) extends over the opposite side of the sheet (7). The skirt (5) is integral with the film (11) which is provided by a conventional adhesive skin patch or wound dressing and is transparent and generally impermeable to moisture. A peel off cover (not shown) is provided over the adhesive skirt (5) and sheet (7) in conventional fashion.

The tube (9) has an internal diameter of 2 mm and an external diameter of 4 mm and is open at both ends. Calibrations in the form of markings (13) are provided along the length of the tube (9). The panel (3) measures 3 cm by 4 cm to give a surface area of 12 $cm^2$.

In use, the panel (3) is placed on a patch of skin (not shown) of a user and secured in position using the adhesive skirt (5) with the tube (9) in an upright orientation and against the skin. The tube (9) thus acts as a spacer and has the effect of lifting the central portion of the sheet (7) off the skin to create two wedge-shaped volumes on either side thereof between the sheet (7) and the skin. Together with the inner volume of the tube (9), these volumes form a reservoir.

As sweat collects in the reservoir, the meniscus level of the sweat aligns with a calibration associated with the sweat measuring device, and can be visually inspected. In this embodiment, the calibrations are in the form of markings (13) on the tube (9), but it will be appreciated that the calibrations can also be in the form of labels, indentations or protrusions on the sweat measuring device (1), or provided on an adhesive strip which may be attached to the sweat measuring device (1). "Calibrations" thus has its widest meaning and includes any means suitable for providing a visual indication of the volume of sweat collected in the reservoir.

Each calibration indicates the volume of sweat collected, and this volume can be used to express the total sweat produced by the user.

The device (1) is typically secured to the upper arm of the user as this area usually provides relatively hairless skin, is convenient to observe and is not subject to bending. However, any suitable area of the body can be used.

The skirt (5) and film (11) prevent the egress of sweat from the patch of skin covered by the panel (3). Sweat produced by the user on the patch of skin becomes trapped under the panel (3). It naturally tends to flow downwards under gravity where it collects in the reservoir. If desired, grooves or ribs could be provided internally of the panel to assist in channelling sweat to the reservoir. The markings (13) on the tube indicate the volume of sweat produced for the known surface area and can be used to estimate the dehydration or total sweat produced by the user.

The volume of the reservoir, in this embodiment, can be simply calculated as the area of the two wedge-shapes minus the solid volume of the tube. Knowing the total body surface area of the person and the area covered by the patch enables the total sweat produced as a function of the volume of sweat in the reservoir to be calculated.

Body surface area (BSA) can be calculated as:

BSA (cm$^2$)=Square root of height (cm)×body weight (kg)/3600

Further, it is accepted that 5% dehydration is severe. For a person of 100 kg, 5% dehydration equates to 5 liters, or 5000 ml, of sweat. If the person has a height of 200 cm the BSA=23600 cm$^2$. At 5% dehydration will be (5000 ml/23600 cm$^2$)=0.2118 ml/cm$^2$. For a 12 cm$^2$ panel, 2.54 ml of sweat will be produced at 5% dehydration. This then would be the practical maximum volume required of the reservoir.

However, it is not required under normal circumstances to measure up to this very dangerous extent of dehydration, and measurement up to 2-3% (1.02-1.52 ml for a 12 cm$^2$ area) will normally be adequate.

The markings (13) will conveniently illustrate % dehydration, for example 0.25%, 0.5%, 0.75% and the like. The user can then use these to determine the volume of replenishing fluid required.

A single configuration of the device can generally be used over a range of body sizes. Estimates using 3 different average sizes of person with a dehydration range of 0-5% show the following:

Size 1
body weight: 100 kg;
height: 200 cm;
BSA: 23600 cm$^2$;
dehydration: 0-5000 ml;
dehydration/cm$^2$: 0-0.2118 ml/cm$^2$
Size 2
body weight: 75 kg;
height: 175 cm;
BSA: 19100 cm$^2$;
dehydration: 0-3750 ml;
dehydration/cm$^2$: 0-0.1963 ml/cm$^2$
Size 3
body weight: 50 kg;
height: 150 cm;
BSA: 14400 cm$^2$;
dehydration: 0-2500 ml;
dehydration/cm$^2$: 0-0.1736 ml/cm$^2$ It can be seen that the maximum, 5%, dehydration per area of the 3 standard persons are so close that for practical purposes the same scale can be used for each person, especially when measuring smaller dehydration %. If desired, however, the device can be individually calibrated for individuals or different body types.

It should be borne in mind that the above calculation of the production of sweat is based on an area of exposed skin on which evaporation can take place. Theoretically the device, or anything else covering the skin, should reduce the production of sweat in that specific area. This can be factored into calculations to determine the appropriate markings.

Also, it is difficult to accurately calculate the volume of sweat retained between the panel and skin through capillary action. However, it appears small enough not to have a practical effect on the accuracy of the device.

It will be apparent that the panel should be fairly rigid so that the covered area of skin remains constant during securing of the device. It also facilitates more accurate measurement during use.

The device of the invention thus permits sweat produced by a user to be measured by collecting sweat in a reservoir from a patch of skin of known area over a period of time, permitting the volume to be visually assessed and expressing the volume collected as a proportion of the sweat produced for the entire body.

Using the measurements of the device the user can fairly accurately assess the volume of fluids lost through sweat and hence the correct volume to replenish. This assists in preventing excessive dehydration or over hydration.

The device lends itself to wide application and can be used with athletes, military personnel, in the medical arena with patients, and with those working or conducting other activities in conditions in which sweating and consequent dehydration occurs.

It will be appreciated that many other embodiments of a sweat measuring device exist which fall within the scope of the invention, particularly regarding the size and configuration of the panel (3) and skirt (5). For example, the sheet (7) can be of any suitable size and could have rounded corners to avoid puncturing the film (11). Also, the tube (9) could be secured within a complementary slot cut into the sheet (7). In this instance, the tube (9) would be shorter than the length of the sheet and ends of the tube could each simply have a diametrically extending slit to engage over the respective ends of the slot, which would consequently be of shorter length than the tube.

The calibrations could be carried on an adhesive strip which can be attached to the device in the appropriate orientation. This permits a number of different calibrations to be supplied with each device to enable the user to customise the device to a degree. The calibrations could be for different body sizes or for indicating different measurements, for example volume of sweat or % dehydration.

Figure 2:
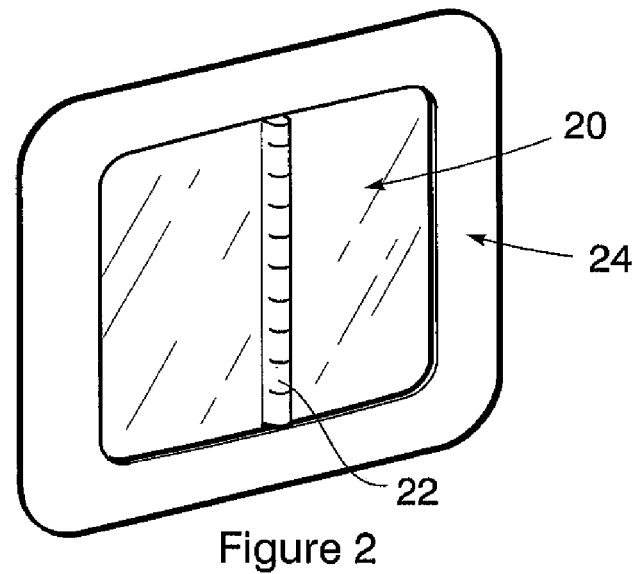
FIG. 2 is perspective view of a second embodiment of a sweat measuring device.

It is, however, not necessary to use a tube. As shown in FIG. 2, the panel (20) can be moulded from a thin, generally planar sheet of a suitable plastics material with a central, trough-shaped reservoir (22) extending along its length, and an integral skirt (24) extending from its periphery. In this embodiment, the planar portion of the panel remains against the skin in use. Only a limited amount of sweat can be retained between the skin and panel before it flows into the reservoir (22) where it can be measured.

Figure 3:
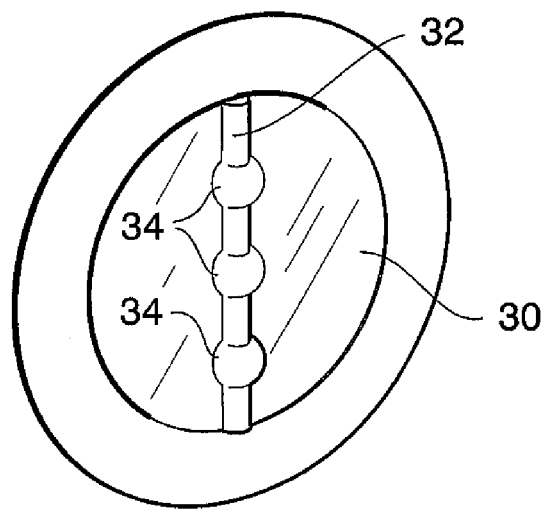
FIG. 3 is perspective view of a third embodiment of a sweat measuring device.

The panel need not be rectangular and can be any suitable shape. As shown in FIG. 3, the panel (30) can be circular. Also in this embodiment, the reservoir (32) is tubular with a number of bulbous, radial enlargements (34) spaced along its length. Each of these bulbs (34) is coated on its interior with a dye which is activated by sweat. The bulbs thus act as calibrations and as sweat progressively reaches and fills the bulbs (34) a strong visual signal is provided. This may be particularly useful during sporting events where it may not always be possible to examine the device carefully.

Alternatively, or in addition, the bulbs (34) could be coated on their interiors with a substance sensitive to the electrolytes contained in the sweat and indicate a high or low sodium level or potassium level. This in turn will indicate to the user the appropriate type of beverage that should be consumed to adjust the level appropriately. To facilitate this the beverages could, for example, be supplied with an appropriate colour. For instance, a red colour in the bulb may indicate low sodium and the appropriate sodium replenishing drink would then also have a red colour.

Figure 4:
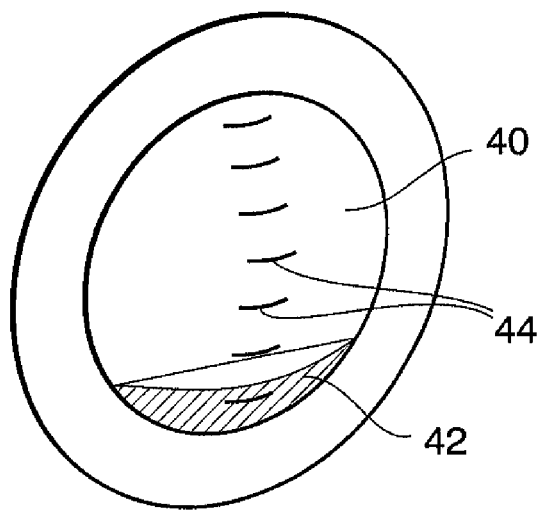
FIG. 4 is perspective view of a fourth embodiment of a sweat measuring device.

As shown in FIG. 4, the panel (40) could be made of a rigid plastics material with an oval periphery and shaped to be outwardly convex. In use, only the edge of the panel (40) is in contact with the skin with the reservoir, in which sweat (42) collects, being formed between the remainder of the panel (40) and the skin. Again, appropriate calibrations (44) will be provided on the panel.

It will be appreciated that the calibrations can have any suitable designation. They could indicate volume, relative volume, % dehydration or even indicate a volume of fluid that should be consumed.

It is also possible to associate with the reservoir other indicators or measurement means. For example, one or more chemical pads or reagents, similar to those used for strip tests, could be provided to indicate the level of salts or other compounds in the sweat. These could be positioned along the reservoir to provide a progressive indication of what is occurring in the body.

It is even possible to associate electronic measurement means with the device and for information to be relayed wirelessly, or otherwise, to receiving devices. It is thus envisaged that it will be possible to provide a small electronic measuring apparatus on the device which transmits information to a watch or similar device worn by the user.

Furthermore, the reservoir could use capillary action rather than gravity. This may provide the advantages of not requiring the device to be secured to the user in a specific orientation and also that a smaller surface area, producing less sweat, be used.

The present invention provides a degree of simplicity over the prior art in that it does not require a material with a wicking action which is reliant on the absorbing abilities of the material, or a chemical reaction to indicate amount of sweat. According to the present invention, the volume of sweat can simply be visually inspected against the calibrations associated with the reservoir. It is thus much more simple and cost effective to manufacture the device of the present invention than those of the prior art. It is also a simple matter to scale the device of the present invention up or down for different body types or to adapt it for different applications by providing sweat impermeable panels of different size and possibly with different calibrations. This aspect is not easily dealt with in the prior art, except possibly with complex electronic systems. Furthermore the device of present invention could be reused by draining off the sweat collected therein.

The invention claimed is:

1. A sweat measuring device for monitoring the extent of dehydration of a user, the device comprising:
a sweat impermeable panel which covers a known area of the user's skin and has a skirt with an adhesive on one side thereof extending about its periphery to enable the panel to be secured to the user's skin to trap sweat produced by the skin under the panel and wherein the panel has at least one tubular spacer having an internal volume, wherein the tubular spacer lifts the central portion of the panel off of the skin to create two wedge-shaped volumes on either side of the tubular spacer, wherein the internal volume of the tubular spacer and the wedge-shaped volumes form a reservoir of a defined volume, wherein the tubular spacer extends in a generally upright direction relative to the ground, in use, and a meniscus level of sweat in the internal volume of the tubular spacer can be visually inspected against calibrations provided along the length of the tubular spacer, wherein the reservoir is configured to collect a volume of sweat that corresponds to between 0.75% and 5% dehydration of the user.

2. A sweat measuring device as claimed in claim 1, wherein the calibrations express total sweat produced by the user as a function of the meniscus level of sweat in the internal volume of the tubular spacer.

3. A sweat measuring device as claimed in claim 1, wherein the panel is stiff.

4. A sweat measuring device as claimed in claim 3, wherein the panel is formed by a plastic member.

5. A sweat measuring device as claimed in claim 1, wherein the skirt extends integrally from the panel.

6. A sweat measuring device as claimed in claim 1, wherein the skirt is integral with an adhesive patch which covers the panel.

7. A sweat measuring device as claimed in claim 1, wherein the calibrations provided along the length of the tubular spacer are in the form of markings.

8. A sweat measuring device as claimed in claim 7, wherein the markings are in the form of labels, indentations or protrusions on the tubular spacer.

9. A sweat measuring device as claimed in claim 1, wherein the tubular spacer has an internal diameter of 2 mm and an external diameter of 4 mm and is open at both ends.

10. A method of measuring sweat produced by a user, the method comprising:
using the sweat measuring device of claim 1 to collect sweat in the reservoir from a patch of skin of known area over a period of time such that the meniscus level of collected sweat can be visually inspected against calibrations provided along the length of the tubular spacer to determine the amount of collected sweat and expressing the amount of collected sweat as a proportion of sweat produced for an entire body associated with the skin to monitor the extent of dehydration of the user.

11. The method according to claim 10, wherein the panel comprises a skirt with an adhesive on one side thereof extending about its periphery to enable the panel to be secured to the user's skin and collect sweat produced by the skin under the panel.

12. The method according to claim 10, wherein the panel is stiff.

13. The method according to claim 10, wherein the panel is formed by a plastic member.

* * * * *